US006472223B1

(12) United States Patent
Stannard et al.

(10) Patent No.: US 6,472,223 B1
(45) Date of Patent: Oct. 29, 2002

(54) METHOD AND SYSTEM FOR CONTINUOUSLY MONITORING AND CONTROLLING A PROCESS STREAM

(75) Inventors: James W. Stannard, Pittsgrove, NJ (US); Kevin Anthony Foster, Kent (GB); David MacDonald Bonnick, East Sussex (GB)

(73) Assignee: United States Filter Corporation, Palm Desert, CA (US)

( * ) Notice: Subject to any disclaimer, the term of this patent is extended or adjusted under 35 U.S.C. 154(b) by 0 days.

(21) Appl. No.: 09/476,556

(22) Filed: Jan. 3, 2000

Related U.S. Application Data

(63) Continuation-in-part of application No. 08/599,274, filed on Feb. 9, 1996, now abandoned, which is a continuation of application No. 07/674,244, filed on Mar. 25, 1991, now abandoned, which is a continuation-in-part of application No. 07/549,994, filed on Jul. 9, 1990, now abandoned.

(51) Int. Cl.[7] .............................................. G01N 31/16
(52) U.S. Cl. ........................ 436/122; 210/746; 210/754; 210/764; 422/62; 436/52; 436/59; 436/125
(58) Field of Search ........................... 436/52, 55, 122, 436/125; 422/62, 81, 82; 210/746, 754, 764

(56) References Cited

U.S. PATENT DOCUMENTS

| 2,396,934 | A | * | 3/1946 | Wallace |
| 2,560,317 | A | * | 7/1951 | Wallace |
| 4,271,149 | A | * | 6/1981 | Winicov |
| 4,440,726 | A | * | 4/1984 | Coulson |
| 5,196,126 | A | * | 3/1993 | O'Dowd |
| 5,275,736 | A | * | 1/1994 | O'Dowd |

OTHER PUBLICATIONS

Finger et al., Development of an on–line zero chlorine residual measurement and control system, Journal of the Water Pollution Control Federation, vol. 57, No. 11 (Nov. 1985), pp. 1068–1073.*

* cited by examiner

Primary Examiner—Jan Ludlow
(74) Attorney, Agent, or Firm—Wolf,Greenfield&Sacks,P.C

(57) ABSTRACT

A method for directly monitoring and controlling a continuous process stream for dechlorination residual is provided. A sample stream to which a dechlorination agent has been added to completely eliminate a residual disinfectant is continuously drawn off. An analyzing agent of iodine is provided by introducing an iodide solution, a chloramine-T solution, and an acetic acid buffer into the sample stream. The reagents quickly react to produce iodine that reacts with any residual disinfectant removal agent residual that may be present. Thereafter, the sample stream is continuously analyzed to determine the amount of unreacted iodine remaining in the process sample. Based on the amount of iodine added to the process sample and the amount of unreacted iodine remaining in the sample after reaction, the amount of dechlorination residual is continuously determined. The amount of dechlorination agent added upstream to the process stream is continuously selectively varied using the determined amount of dechlorination residual present in the process sample.

11 Claims, 4 Drawing Sheets

METHOD AND SYSTEM FOR CONTINUOUSLY MONITORING AND CONTROLLING A PROCESS STREAM

This application is a continuation-in-part of application Ser. No. 08/599,274, filed Feb. 9, 1996 now abandoned, which is a continuation of application Ser. No. 07/674,244, filed Mar. 25, 1991, now abandoned, which is a continuation-in-part of application Ser. No. 07/549,994, filed Jul. 9, 1990, now abandoned.

BACKGROUND OF THE INVENTION

1. Field of the Invention

The present application is directed to a method and system for continuously monitoring and controlling a process stream for a dechlorination residual and, in particular, to a method and system for continuously monitoring and controlling a process stream for a dechlorination residual using chloramine-T.

2. Description of the Related Art

Chlorine is commonly used to disinfect sewage treatment plant process streams and for biofouling control in cooling systems. Because chlorine is such a highly effective disinfecting/oxidizing agent, any chlorine unused in the process is just as effective in destroying aquatic life.

In order to eliminate or substantially remove the residual chlorine from a process stream, a dechlorination agent or device is often used. Typically, sulfur dioxide ($SO_2$) is added to the process stream to react quantitatively with the chlorine residual. If $SO_2$ is added in excess of the amount of chlorine residual in the process stream, the chlorine will be completely eliminated.

The amount of unreacted dissolved $SO_2$ (i.e., dechlorination residual) remaining in the process stream is preferably maintained at low, but positive, concentration to ensure chlorine residual removal and minimize oxygen consumed. This sort of treatment not only protects aquatic life, but results in more efficient use of the $Cl_2$ and $SO_2$ reagents added to the process stream. However, there are no completely acceptable methods or systems available for directly monitoring and controlling the amount of dechlorination residual in a continuous process stream to which a chlorine disinfectant/oxidant has been previously added.

One example of a method for determining the concentration of a chemical constituent in a fluid is disclosed in U.S. Pat. No. 2,560,317. The method disclosed is particularly well-suited for detecting the concentration of residual chlorine in a process stream. The method involves the removal of chlorine from a process stream sample stream by passing the sample through an activated carbon bed and thereafter adding chlorine at a variable and determinable rate to compare the relative concentrations of chlorine in that stream to the relative concentration of chlorine in an untreated process sample stream. When the comparison is brought to a zero difference, by adjusting the rate of chlorine addition, the determinable rate at which chlorine is added to the chlorine free sample stream is an exact measure of the amount of chlorine in the process stream. Iodine is identified as a suitable substitute for chlorine when it is added to the chlorine free stream. Although this method allows the amount of residual chlorine to be measured, it is completely silent as to measuring a dechlorination residual in the process stream.

Other examples of methods for measuring and controlling on-line zero chlorine residual are disclosed in Finger, et al., "Development Of An On-Line Zero Chlorine Residual Measurement And Control System." J. Water Pollution Control Fed., Vol. 57, No. 11, 1068 (1985). Finger et al. recognize that there are no techniques available to directly monitor or control zero chlorine residuals nor are there any continuous analytical techniques available to monitor dechlorination (i.e., dissolved $SO_2$) residuals.

Finger et al. identify a feed-forward system that incorporates an effluent flow signal and a chlorine residual signal which are measured immediately before the dechlorination point. Finger et al. also identify a feedback residual control system that biases the dechlorination sample with large volumes of gaseous chlorine or liquid hypochlorite reagents before the dechlorination sample is analyzed. However, Finger et al. argue that both of these systems are deficient because they depend on precise sample and biasing reagent flows. Sample biasing with chlorine or hypochlorite is also subject to chemical reaction interferences with other contaminants (e.g., ammonia) which may be present in the process stream.

In an attempt to overcome these problems, Finger et al. provide a complex feedback approach wherein a dechlorination effluent is biased with the chlorinated effluent to form a sample that can be measured with conventional chlorine analyzers. The effluent flows are held at a 1:1 ratio with constant-head tanks and the chlorine residual of the dechlorination effluent is electronically calculated from the measured residuals in the chlorine and dechlorinated effluent based on the equation:

$$C_{post} = 2C_{meas} - C_{pre}$$

wherein:

$C_{post}$=the chlorine residual of the dechlorinated effluent;

$C_{pre}$=the chlorine residual of the effluent prior to dechlorination; and $C_{meas}$=the chlorine residual of the 1:1 mixture of pre- and post-dechlorination effluents.

The method requires two analyzers to be used to determine the amount of chlorine residual in the dechlorinated effluent. Excessive instrumentation is necessary because the variability of the residual measuring technique must be minimized to ensure control within regulatory limits. The dechlorinated residual is calculated and controlled from the summation output of the two residual analyzers.

All of the systems discussed above are expensive to install and have substantial operational costs associated with maintenance, sample pumping, and reagent costs. These systems are often inherently unstable, producing measurement errors that typically exceed safe regulatory residual limits by several orders of magnitude. This is especially undesirable since dechlorination control continues to be the subject of more stringent environmental regulations.

SUMMARY OF THE INVENTION

The invention comprises methods and systems for monitoring and controlling the amount of a disinfectant removing agent, for example, sulfur dioxide, in a continuous process stream. The disinfectant removing agent is added in excess to the process stream to reduce or eliminate a disinfectant residual which has previously been added to the process stream.

The method of the present invention comprises continuously drawing off a sample of the process stream and continuously adding an iodine analyzing agent to the sample in an amount sufficient to completely react with the residual disinfectant removing agent and leave an unreacted amount of analyzing agent or, in the case of incomplete disinfectant removal, to add to the disinfectant residual. The iodine is provided by a reaction between two reagents, an iodide and chloramine-T ($C_7H_7ClNO_2S^-Na^+$). The two reagents are introduced into the sample stream which is maintained at a pH from about 3.5 to about 4.5 through the introduction of a third reagent, an acid. The three reagents may be introduced into the sample stream separately or together and the time required to react, i.e., to produce the iodine, is minimal. Thereafter, the sample is continuously analyzed to determine the amount of unreacted iodine, or iodine plus disinfectant, remaining in the sample. Based on the amount of iodine added and the amount of unreacted iodine remaining in the sample after reaction, the amount of residual disinfectant removing agent or disinfectant residual is determined. Using the determined amount of residual disinfectant or disinfectant removing agent, the amount of disinfectant removing agent that is added to the process stream is controlled.

BRIEF DESCRIPTION OF THE DRAWINGS

Preferred, non-limiting embodiments of the present invention will be described by way of example with reference to the accompanying drawings, in which.

DETAILED DESCRIPTION OF THE INVENTION

Figure 1:
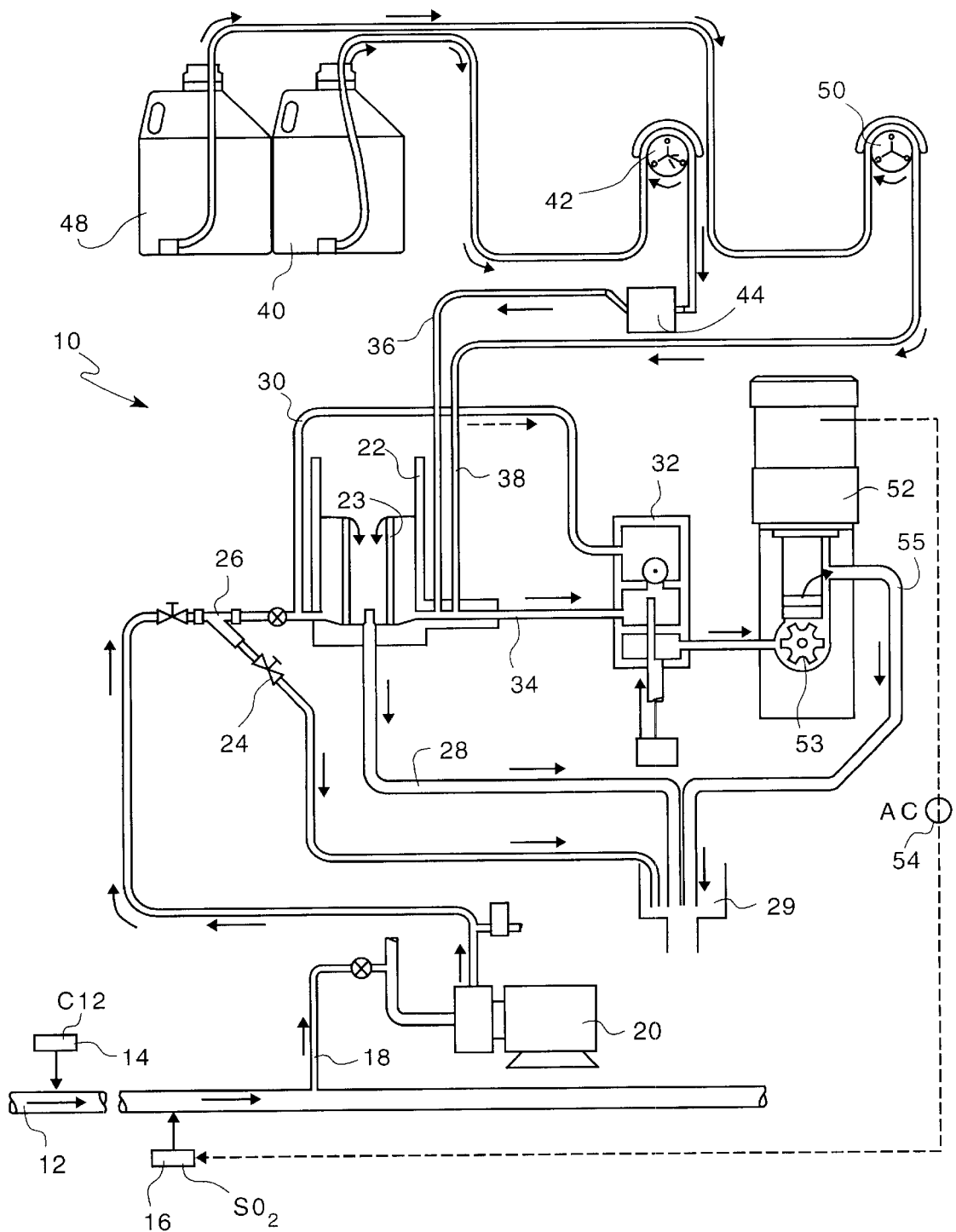
FIG. 1 is a schematic illustration of an embodiment of the system of the invention.
Figure 2:
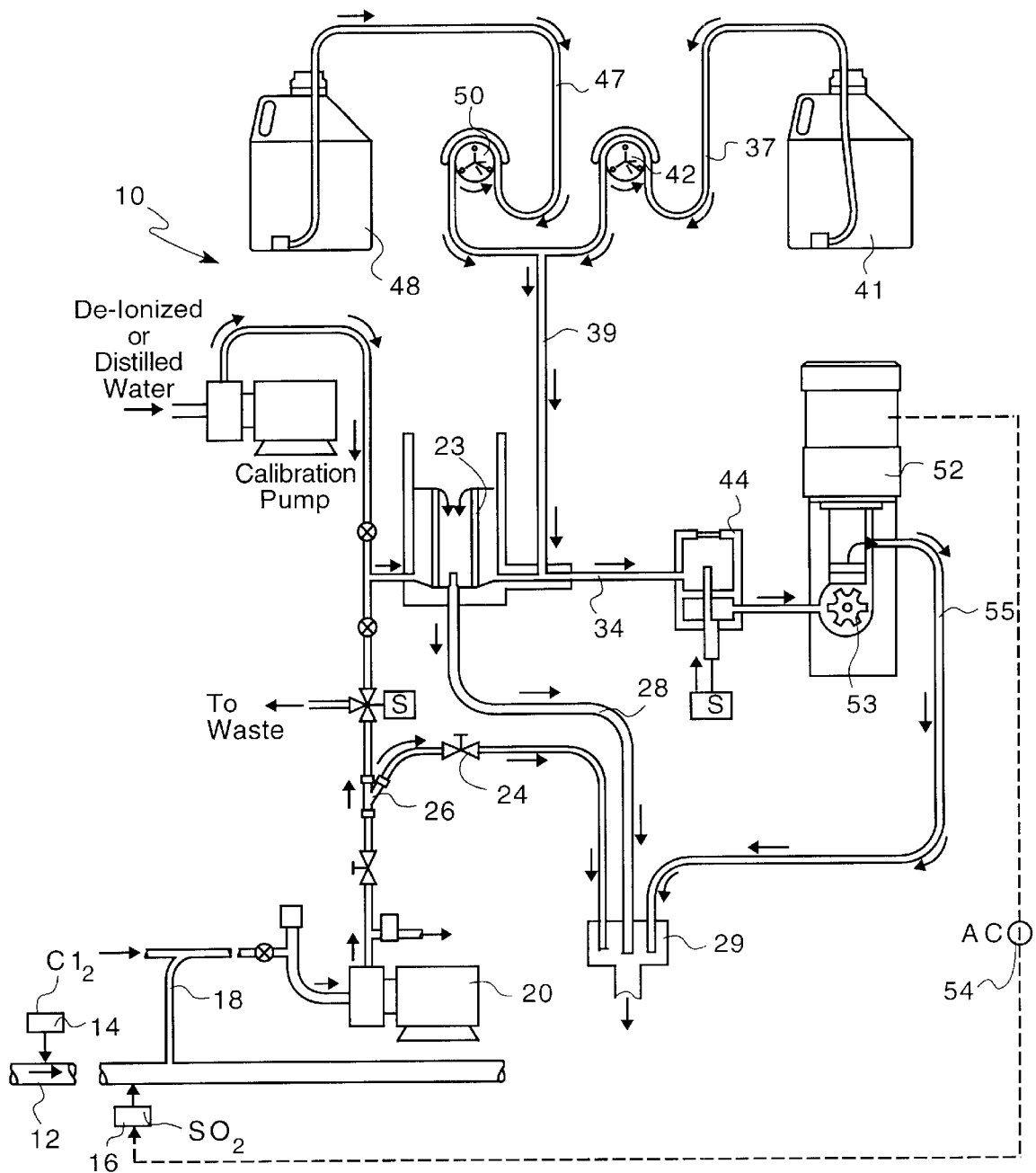
FIG. 2 is a schematic illustration of another embodiment of the system of the invention.

Referring now to the drawings, wherein like numerals indicate like elements, there is shown in each of FIGS. 1 and 2 a system 10 for monitoring and controlling the amount of dechlorination residual within a process stream 12. Dechlorination is defined here as the complete or partial removal of any oxidant, including chlorine, by the controlled addition of a reducing agent.

In FIG. 1, once the process stream 12 is dechlorinated, the amount of dechlorination residual (i.e., unreacted $SO_2$) is determined by continuously withdrawing a sample stream 18, downstream of the $SO_2$ source 16. The sample is withdrawn by pump 20 and transported to constant level box 22.

Typically, a sample flow of about 1 to 2 gpm will be adequate for monitoring and controlling the amount of dechlorination residual in the process stream. Excess sample is used to clean the filter element in Y-fitting 26. Excess sample is removed from system 10 by opening valve 24 just downstream of Y-fitting 26 and by collecting the overflow from constant level box 22.

Excess sample in constant level box 22 pours over internal tube 23 and into stream 28. The excess sample is collected in drain 29 and, preferably, returned to process stream 12. The sample may also be bypassed around constant level box 22 by stream 30 to orifice 32, described in more detail hereinafter.

The constant level box 22 provides a constant head of dechlorinated process sample. The dechlorinated process sample held in constant level box 22 is then passed through stream 34 to orifice 32. In the embodiment illustrated in FIG. 1, as the dechlorinated process leaves constant level box 22 under the force of gravity, a continuous stream of analyzing agent solution 36, different from the process disinfecting agent, is introduced in an amount sufficient to completely react with the dechlorination residual in the dechlorinated sample stream and leave an unreacted amount of analyzing agent.

Any suitable analyzing agent can be employed when practicing the present invention. Examples of suitable analyzing agents include, but are not limited to: iodine, bromine, chlorine gas, hypochlorite solutions, and the like and/or mixtures thereof. The presently preferred analyzing agent is iodine. Unlike chlorine gas or hypochlorite solutions, iodine reacts much more slowly with ammonia which is commonly found in sewage treatment plant process stream.

While iodine is the presently preferred analyzing agent, any suitable source of iodine can be employed when practicing the present invention. For example, the iodine can be derived from an iodine source (e.g., item 40 as illustrated in FIG. 1), from a reaction between iodate and iodide, or from a reaction between chloramine-T and iodide. A specific manner in which iodine can be derived from a chemical reaction between an iodate and an iodide will be discussed later.

Referring again to FIG. 1, in one embodiment of a preferred practice, an iodine solution stream 36 is drawn from an iodine source 40 and precisely metered by a peristaltic pump 42 in order to introduce the iodine solution into the dechlorinated process sample at a fixed concentration and rate. Based on the concentration and flow rate of the iodine solution, the exact amount of iodine is readily calculated. The iodine solution stream 36 is passed through a gas purger 44 in order to remove any gas bubbles which may be contained within stream 36. As will be described in greater detail later, gas purger 44 contains a hydrophobic membrane for releasing any gas bubbles which may be present in stream 36.

Also, in the embodiment illustrated in FIG. 1, a separate buffering solution stream 38 is employed to introduce the buffering solution used in the downstream biasing process into the dechlorinated sample stream. The buffering solution is added to the system via stream 38 to stabilize the pH of the mixture. The buffering solution stream 38 is drawn from a buffering solution source 48 and metered by a peristaltic pump 50 in order to introduce the buffering solution to the dechlorinated process sample at a determinable rate.

Following the addition of the iodine solution and buffering solution to the dechlorinated process sample, a chemical reaction takes place between the dechlorination residual ($SO_2$) and the iodine.

The process sample with $SO_2$ and $I_2$ completely reacted is passed through orifice 32 and into analyzer 52. Orifice 32 acts to control the flow rate of the reaction treated process sample into analyzer 52. The analyzer 52 preferably contains an amperometric cell which allows the amount of unreacted $I_2$ to be determined through direct measurement. Analyzer 52 is described in greater detail hereinafter and is also the subject of U.S. Pat. No. 4,822,474, the contents of which are incorporated herein by reference.

Based on the amount of unreacted $I_2$ measured by analyzer 52, and the known metered amount of $I_2$ added in iodine solution stream 36, the amount of $SO_2$ (i.e., dechlorination residual) within process stream 18 can be calculated. Based on the calculated amount of dechlorinated residual within process sample stream 18, the amount of $SO_2$ introduced upstream in process stream 12, via $SO_2$ introduction means 16, is controlled by controller 54. After the analysis is complete, the analyzed sample is then exhausted to drain 29 through stream 55 for collection and removal from system 10.

Those skilled in the art will recognize that pump 20, constant level box 22, orifice 32, peristaltic pumps 42 and 50, analyzer 52, and controller 54 are all commonly used process equipment. As a result, a detailed description of their structure and operation is not necessary to understanding the method and system of the invention.

Another embodiment of a presently preferred practice is illustrated in FIG. 2. As in FIG. 1, FIG. 2 also illustrates a system 10 for monitoring and controlling the amount of dechlorination residual within a process stream 12, wherein iodine is used as the biasing agent. Three of the major differences between the embodiments illustrated in FIGS. 1 and 2 are as follows: (a) the manner in which the iodine and the buffering solutions are introduced into system 10, (b) the origin of the iodine solution and (c) the location of the gas purge valve 44.

For example, in FIG. 1, the iodine employed in the biasing process originates from iodine source 40. There, the iodine is supplied into process stream 34 via stream 36. Also in FIG. 1, the buffering solution is supplied into process stream 34 via stream 38. On the other hand, in FIG. 2, both the iodine and the buffering solutions are supplied into process stream 34 through stream 39.

In the specific embodiment illustrated in FIG. 2, the iodine employed as the biasing agent is derived from a chemical reaction between an iodate, an iodide and an acidic solution. When practicing this embodiment of the invention, the acidic solution, the iodate and the iodide are metered into a reaction chamber or zone 39. This reaction chamber/zone is located upstream of the point where the resulting iodine solution will enter process stream 34.

One method of introducing the reaction components into the reaction chamber/zone comprises introducing the acidic solution, the iodate and the iodide through separate streams such that the components are not combined with one another until they enter the reaction chamber/[]zone. Another manner in which these reaction components can be introduced into the reaction chamber/zone comprises introducing the acidic solution through a first stream and introducing a combination of the iodate and iodide solutions through a second stream (e.g., see FIG. 2).

If the iodate and iodide components are introduced into the reaction chamber/zone as an iodate/iodide solution, the iodate/iodide solution is preferably maintained at a certain level of alkalinity such that the iodate does not begin to react with the iodide to produce a greater than minimal amount of iodine. Typically, if the iodate and iodide are supplied to the reaction chamber/zone as a common solution, the pH of the iodate/iodide solution should be maintained at a value of at least about 9.5. For even improved stability, the pH of the iodate/iodide solution should be maintained at a value of at least about 10.5, preferably, at a value of at least about 11.5.

Any suitable means can be employed to maintain the iodate/iodide solution at the appropriate level of alkalinity. The presently preferred method is to employ a suitable metal hydroxide which will not adversely affect the biasing process of the present invention. Examples of suitable metal hydroxides which can be employed for this purpose include, but are not limited to: potassium hydroxide, sodium hydroxide, magnesium hydroxide, and the like, and/or any combination thereof. It should be noted that, if the iodate and iodide reaction components are supplied to the reaction chamber/zone via separate and distinct streams such that they do not interact with one another until after entering the reaction zone 39, it is not necessary to maintain a particular level of alkalinity.

In the embodiment illustrated in FIG. 2, the iodate and iodide components are supplied as a common solution via iodate/iodide solution source 41. Specifically, in FIG. 2, the iodate/iodide solution is metered into stream 39 (which acts as the reaction zone) by peristaltic pump 42 via stream 37.

At the same time, the acidic solution is metered from source 48 by peristaltic pump 50, along stream 47, also into stream 39. While the acidic buffering solution and the iodate/iodide solution are passing within stream 39 (i.e., the reaction zone), they are reacting with one another to form an iodine-containing reaction product. This reaction product is then fed into sample stream 34 for biasing purposes in accordance with the present invention.

If the embodiment is employed wherein the iodine source is derived from a reaction between an iodate, an iodide and an acidic solution, any suitable iodate can be employed. Examples of suitable iodates include, but are not limited to, metal-iodates, such as potassium iodate, sodium iodate and the like.

Regarding the iodide employed as a reaction component of this latter embodiment, any suitable iodide can be employed which, when in the presence of an acidic environment, will react with the iodate to produce iodine. Examples of suitable iodides include, but are not limited to, metal iodides, such as potassium iodide, and rubidium iodide and the like.

Regarding the acidic solution employed as a reaction component of this latter embodiment, it must be able to react with the iodate and iodide to produce an iodine containing reaction product. Moreover, it must not adversely affect the operation of the downstream biasing process of the present invention.

Any such suitable acidic solution can be employed when practicing this embodiment of the invention. Typically, organic or inorganic acids can be employed for this purpose. Examples of such suitable acidic solutions include, but are not limited to, acetic acid, sulfuric acid, hydrochloric acid, and the like and/or any combination thereof. The presently preferred buffering agent comprises acetic acid.

Since the buffering solution employed in the process of this invention is acidic, it can also be used as the acidic solution reaction component. Here, an excess amount of the buffering solution would be introduced into reaction zone 39.

When practicing the embodiment of the invention wherein the iodine is derived from a reaction between an iodate, an iodide and an acidic solution, the flow rate and concentration of the iodate solution, the iodide solution, the iodate/iodide solution and/or the acidic solution depend, in part, upon many different variables. Examples of some variables which should be taken into consideration when determining flow rates and/or concentrations include, but are not limited to, flow rate of sample solution exiting constant level box 22 through stream 34, specific composition of acidic solution, pH of acidic solution, pH of iodate solution, pH of the iodide solution, time needed for the specific iodate, the specific iodide, and the specific acidic solution to react with one another and form an iodine-containing reaction mixture, the amount of iodine necessary for the specific biasing process, the normality of the iodine necessary for the specific biasing process, the amount and/or pH of the buffering solution necessary for the specific biasing process, and the like. After understanding this embodiment of the present invention, a skilled artisan should be able to take the above variables into consideration and determine the optimum flow rates and concentrations of the specific iodate, the specific iodide and the specific acidic solutions to be employed.

Figure 4:
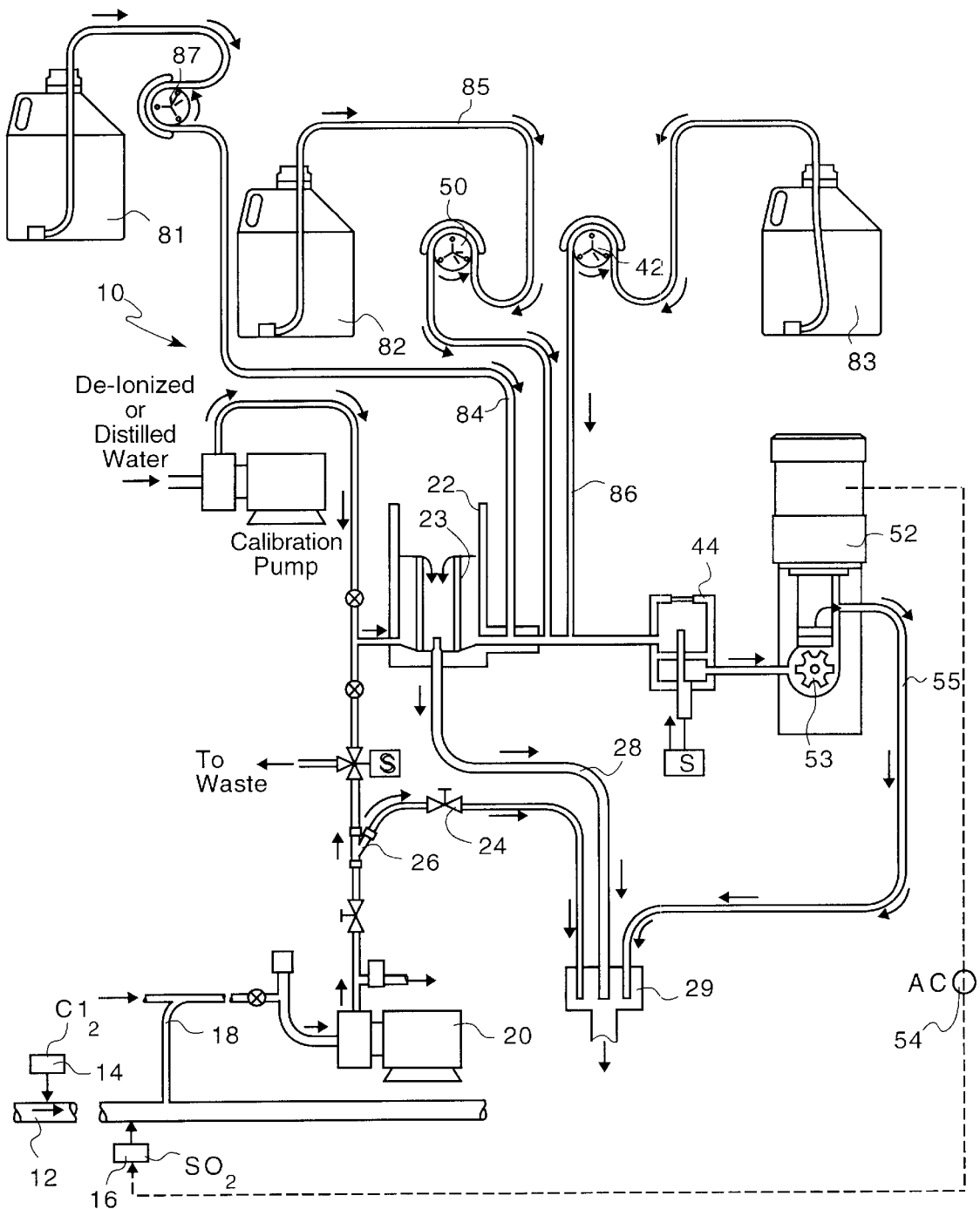
FIG. 4 is a schematic illustration of another embodiment of the system of the invention.

In a preferred embodiment, shown for example in FIG. 4, three different reagents are added directly to the sample fluid stream without the use of a reaction chamber/zone. The reagents may also be mixed together in any combination prior to their introduction into the sample stream. In this embodiment, the three reagents 81, 82, and 83 may enter the sample stream by way of streams 84, 85 and 86 independently, prior to its introduction into the analyzer 52. Flow of the three reagents may be controlled by pump 42, pump 50 or pump 87. Alternatively, one peristaltic pump (not shown) with three channels may be used to pump the three reagents, or a four channel pump may be used to pump the three reagents and the sample. If a four channel pump, or similar is used, the constant level cup 22 may be eliminated. One of the preferred reagent groups that may be used with this embodiment of the invention includes chloramine-T (N-chloro-4-methylbenzenesulfonamid sodium salt) in combination with an iodide and an acidic buffer. The iodide may be in the form of potassium iodide and the acidic buffer may be acetic acid. Preferably, the iodide is added at a 100% stoichiometric excess in relation to the amount of chloramine-T. The excess amount is available to react with disinfectant in the event that excess disinfectant remains in the sample. This may allow for the measurement of disinfectant directly should the amount of disinfectant exceed the level of disinfectant removing agent. Each of the reagents may be added directly and separately to the sampling stream, and a separate reaction zone is not required in order for the reagents to adequately react. As this combination leads to faster liberation of iodine than many other embodiments, it may provide for a stable and fast analysis. Any dechlorination agent that may be in the sample stream reduces either the chloramine-T or the iodine, and any unreacted chloramine-T converts iodide to iodine which can then be accurately measured at the electrode. The concentration of iodine produced may be the same as in other embodiments, for example, 0.00679 N. The order of the sample reagents introduction into the stream is not critical. Chloramine-T is not limited to use with chlorinated samples and may be useful with any disinfectant/oxidant, for example, bromine, ozone or permanganate.

This "chloramine-T" embodiment may provide for a more stable analytical reading than other reagent combinations because it is believed that aging iodine may set up an $I_3$ equilibrium on the electrode surface that results in observed noise factors of about 5%. Because chloramine-T provides for a much faster liberation of iodine than does iodate, the noisy equilibrium on the electrode surface may be reduced to undetectable levels.

The gas purger 44 of FIG. 1 is a sealed container of cylindrical construction although other shapes are permissible. A stream enters the purger through an inlet and exists from an outlet. Closely fitted within the gas purger is a hydrophobic membrane which is permeable to the gas bubbles in the stream. The membrane allows any gas bubbles which are present within the iodine solution of the stream to be removed before the iodine solution is introduced into the dechlorinated process sample. The trapped gas bubbles are then exhausted to the atmosphere through a vent. The gas purger ensures that the iodine solution within the stream is void of gas bubbles so that the exact amount of iodine added to the dechlorinated process sample is known. Gas bubbles, which may be present in the stream, will produce an inaccurate measure of the amount of iodine in stream 36. Ultimately, this condition will result in an inaccurate measurement for the amount of dechlorination residual within the process sample.

It should be noted that, although not illustrated, it is within the scope of this invention to employ a gas purger along stream 39 of FIG. 2.

Figure 3:
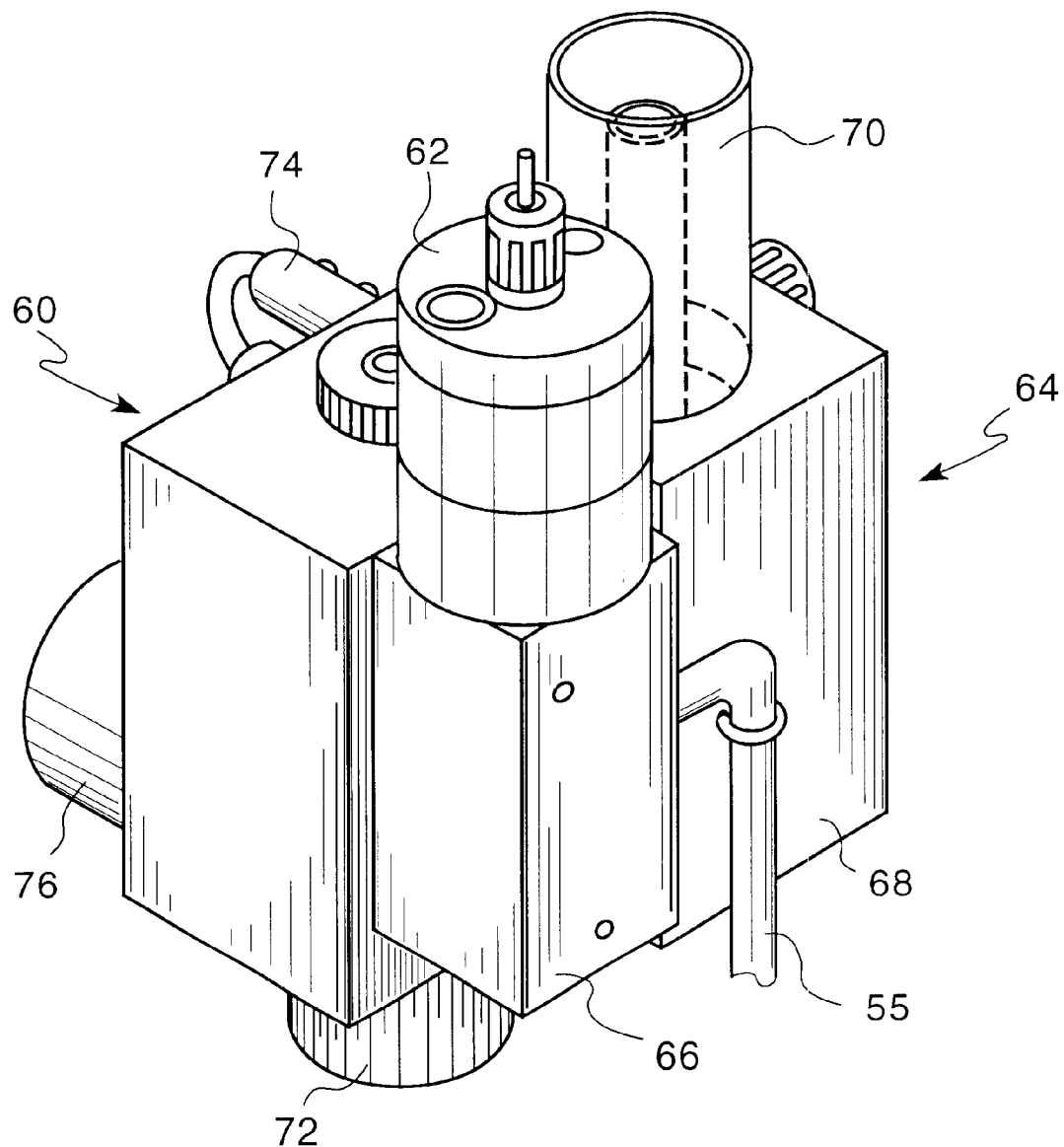
FIG. 3 is a plan view of a residual analyzer assembly used to determine the amount of dechlorination residual in a process sample.

Referring now to FIG. 3, the internal assembly of analyzer 52 is shown in greater detail. Residual analyzer assembly 60 comprises a probe portion 62 and a working fluid sampler system 64. The working fluid sampler system 64 includes a probe block 66 which supports the probe 62 and a flow block 65 which defines the flow passageways of the sampler system 64. Preferably, an amperometric type probe utilizing bare or exposed electrodes is selected. A constant level box 70 maintains the sample to be analyzed at a constant head. An orifice-cleaning mechanism 72, an adjustable flow delay 74, and an impeller mechanism chamber 76 also make up assembly 60. The various internal passageways direct a sample of the flow through fluid sampler system 64 for analyzation by probe 62 and then exhaust the flow for collection in drain 29, via stream 55.

The invention will still more fully be understood from the following examples. These examples are intended to illustrate embodiments of the invention wherein the iodine source is derived from a reaction between an iodate, an iodide and an acidic solution. It should be noted that these examples are in no way intended to limit the scope of this invention.

EXAMPLE I

The preparation of iodate/iodide solutions useful as reaction components to produce an iodine-containing reaction product was demonstrated. Specifically, two methods of preparing an iodate/iodide solution such that, when the solution is subjected to an acidic environment, the resulting iodine solution produced will have a normality of 0.00679 N.

Preferred Method

An iodate solution was prepared by dissolving 0.92 grams of potassium iodate in one-half gallon of distilled water at room temperature and standard pressure while being stirred for 15 minutes. An iodide solution was then prepared by dissolving 160 grams of potassium iodide and 6 grams of potassium hydroxide in one-half gallon of distilled water.

The iodate and iodide solutions were then mixed and stirred at room temperature and standard pressure to produce an iodate/iodide solution. The pH of the iodate/iodide solution was greater than 11.5.

When the iodate/iodide solution was mixed with acetic acid, the reaction components reacted with one another to produce, among other things, an iodine solution having a normality of 0.00679 N.

Alternate Method

An alkaline solution was prepared by dissolving 10 grams of potassium hydroxide in 1 liter of distilled water. Thereafter, 160 grams of potassium iodide and 3.27 grams of iodine crystals were dissolved in the alkaline solution.

The reaction mixture was then permitted to stand for approximately 24 hours to produce an iodate/iodide solution. When the iodate/iodide solution was mixed with acetic acid, the reaction components reacted with one another to produce, among other things, an iodine solution having a normality of 0.00679 N.

EXAMPLE II

The operation of the invention using a chloramine-T reagent system of the present invention was demonstrated. A chloramine-T solution was made by dissolving approximately 1.84 g chloramine-T (N-chloro-4-methylbenzenesulfonamid sodium salt, $C_7H_7ClNO_2S^-Na^+$) into 1 gallon distilled water. This reagent was fed into the sample stream at a rate of approximately 1 mL per 200 mL of sample.

A second reagent containing acetic acid was also fed into the sample stream at a rate and concentration that was adequate to result in a sample stream pH of between abut 3.5 and 4.5. A third reagent, a solution of potassium iodide (KI), was fed into the sample stream as well. The KI solution was produced by dissolving 250 g KI into 1 gallon of water and was fed into the sample stream at the same rate of 1 mL per 200 mL of sample. In this EXAMPLE, all three reagents were pumped through different channels of the same peristaltic pump and then back through the same pump on a fourth channel that pumps the sample. In this way, one pump was used to introduce reagents as well as to move the sample to the analyzing cell.

During the analytical procedure, a known bias of about 0.75 ppm iodine, measured as chlorine, was added to the sample to react with an expected concentrated of sulfite of about 0.5 ppm. The known bias was then accounted for when the actual concentration of sulfite in the sample was calculated. Any sulfite readings (i.e., when the reading from the analyzer was less than the bias amount) were multiplied by 0.9 to correct for the weight difference between chlorine and sulfite.

The output from the analyzer was significantly more stable than that obtained when using alternative sources of iodine and demonstrated a noise level of less than about 1% of the signal.

The conditions in the foregoing description are for illustration only and should not be construed as limiting the scope of the invention. The present invention may be embodied in other specific forms without departing from the spirit or essential attributes thereof, and accordingly, reference should be made to the appended claims, rather than to the foregoing specification, as indicating the scope of the invention.

What is claimed is:

1. A method for determining the amount of residual disinfectant removing agent in a process stream, comprising the steps of:
   (a) continuously drawing off a sample of said process stream;
   (b) adding an iodide solution to said sample;
   (c) adding a chloramine-T solution to said sample;
   (d) producing iodine in sufficient concentration to react with any residual disinfectant removing agent in the sample;
   (e) determining the quantity of unreacted iodine in the sample; and
   (f) determining the amount of residual disinfectant removing agent in the sample.

2. The method of claim 1 wherein the process stream has been disinfected with chlorine.

3. The method of claim 1 wherein the disinfectant removing agent is sulfur dioxide.

4. The method of claim 1 wherein the pH of the sample is adjusted to a range of about 3.5 to 4.5.

5. The method of claim 1 wherein the chloramine-T, the iodide and a buffer are introduced directly into the sample stream.

6. The method of claim 5 wherein the buffer comprises acetic acid.

7. The method of claim 6 further comprising the addition of a biasing amount of disinfectant to the sample.

8. The method of claim 7 wherein the biasing amount is equal to about 150% of an expected amount of disinfectant removing agent residual.

9. The method of claim 6 further comprising using the determined amount of residual disinfectant removing agent to vary the amount of disinfectant removing agent added to the process stream.

10. The method of claim 1 wherein the iodide is added at a concentration of at least about a 100% stoichiometric excess.

11. The method of claim 1 wherein the iodine is produced at a concentration of about 0.00679 N.

* * * * *